(12) United States Patent
Root et al.

(10) Patent No.: US 7,455,649 B2
(45) Date of Patent: Nov. 25, 2008

(54) ABDOMINAL TISSUE SUPPORT FOR FEMORAL PUNCTURE PROCEDURES

(75) Inventors: Howard Root, Excelsior, MN (US); James Quackenbush, Chanhassen, MN (US); Max Ortiz, Avondale, AZ (US)

(73) Assignee: Vascular Solutions, Inc., Minneapoils, MN (US)

( * ) Notice: Subject to any disclaimer, the term of this patent is extended or adjusted under 35 U.S.C. 154(b) by 302 days.

(21) Appl. No.: 11/029,908

(22) Filed: Jan. 5, 2005

(65) Prior Publication Data

US 2006/0149177 A1    Jul. 6, 2006

(51) Int. Cl.
*A61F 13/00* (2006.01)
*A61F 5/37* (2006.01)
*A61B 19/00* (2006.01)

(52) U.S. Cl. ........................... 602/19; 128/849
(58) Field of Classification Search ............ 602/4, 602/19; 450/1, 155; 128/869, 873, 874, 128/96.1, 99.1, 100.1, 101.1; 2/311, 312, 2/330, 338, 327, 328
See application file for complete search history.

(56) References Cited

U.S. PATENT DOCUMENTS

| | | | |
|---|---|---|---|
| 572,465 A | 12/1896 | Woolfolk et al. | |
| 811,167 A | 1/1906 | Paddock | |
| 933,610 A | 9/1909 | Yanowsky | |
| 1,529,937 A | 3/1925 | Turcotte et al. | |
| 1,565,808 A | 12/1925 | Levy | |
| 1,983,636 A | 12/1934 | Palkens | |
| 2,104,699 A | 1/1938 | O'Dell | |
| 2,282,021 A | 5/1942 | Benningfield | |
| 2,327,671 A | 8/1943 | Rupprecht | |
| 2,719,568 A | 10/1955 | Webb | |
| 2,840,822 A | 7/1958 | Ericsson | |
| 3,101,718 A | 8/1963 | Rocker | |
| 3,103,316 A | 9/1963 | Schaal | |
| 3,116,735 A | 1/1964 | Geimer | |
| 3,452,362 A | 7/1969 | Korolick et al. | |
| 3,554,190 A | 1/1971 | Kaplan | |
| 4,530,122 A | 7/1985 | Sanders et al. | |
| 4,782,535 A | 11/1988 | Yewer, Jr. et al. | |
| 4,822,317 A | 4/1989 | Wimmer | |
| 4,866,789 A | 9/1989 | Dorm | |
| 4,981,307 A | 1/1991 | Walsh | |
| 5,007,412 A | 4/1991 | DeWall | |
| 5,040,524 A | 8/1991 | Votel et al. | |
| 5,148,549 A | 9/1992 | Sydor | |
| 5,928,059 A | 7/1999 | Wicks | |
| 6,071,175 A | 6/2000 | Working, III | |
| 6,073,823 A * | 6/2000 | Gordon | 224/661 |
| 6,146,345 A | 11/2000 | Mignard | |
| 6,159,070 A | 12/2000 | Schwartz et al. | |
| 2004/0067716 A1 | 4/2004 | Wakefield | |

* cited by examiner

*Primary Examiner*—Kim M Lewis
(74) *Attorney, Agent, or Firm*—Patterson, Thuente, Skaar & Christensen, P.A.

(57) ABSTRACT

An abdominal tissue support for supporting excess abdominal adipose tissue away from the femoral crease to facilitate the maintenance of a sterile field for femoral puncture procedures. The abdominal tissue support may generally include a waist belt, at least one support apron affixed to the waist belt and a strap arrangement. The abdominal tissue support may also include a movable support apron slidable along the length of the waist belt. The strap arrangement may be securable at a patient's shoulders or to a fixture located near the patient's head.

25 Claims, 7 Drawing Sheets

ABDOMINAL TISSUE SUPPORT FOR FEMORAL PUNCTURE PROCEDURES

FIELD OF THE INVENTION

The present invention relates generally to the field of maintaining a sterile field for surgical procedures. More particularly the invention relates to supporting parts of the body clear of the sterile field and the femoral crease while performing a femoral puncture procedure.

BACKGROUND OF THE INVENTION

Many medical procedures entail inserting a catheter into an artery to gain access to the body's vasculature to perform various medical or surgical procedures. A preferred location for accessing the femoral artery is at the femoral crease where the upper thigh joins the groin. In order to avoid introducing pathogenic microorganisms into the body's vasculature or blood stream, it is necessary to maintain a sterile field in the vicinity of the puncture that is made to access the femoral artery.

It is estimated that about forty million Americans are obese and an even larger number are overweight. Patient's that are obese are at higher risk of vascular disease including coronary artery disease as well as other health problems. An increasing number of patients that present for procedures that utilize a femoral puncture are overweight or obese.

Between five and fifteen percent of patients who present for femoral puncture procedures to insert a catheter are obese or overweight to the point that they have excess abdominal tissue that covers the artery access site. In order to gain access to the femoral artery at the femoral crease and to maintain a sterile field for the femoral puncture it is necessary that the excess abdominal tissue be repositioned away from the femoral crease. Current procedure in preparing the patient for femoral puncture calls for taping the excess abdominal tissue with surgical tape in an attempt to move it away from the femoral access site. Utilizing surgical tape to support the excess abdominal tissue requires preparing the skin for application of the tape. Preparation can include shaving hair from the skin in the areas where the tape must adhere to the body. When the procedure is completed the tape must be removed from the patient's body, which can be painful for the patient. Because the effectiveness of this approach will necessarily vary from patient to patient, the potential for the tape to give way during the surgical procedure is a significant problem.

Generally when there is excess abdominal tissue that must be moved away from the access site, two caregivers must work together to lift the excess tissue and apply the tape so as to allow access to the femoral artery. The requirement of two caregivers is inefficient and also requires that two care providers initially prepare the patient by taping the abdominal tissue and then proceed to scrub to maintain the sterile field. An improved method and apparatus for supporting abdominal tissue away from the femoral puncture site will provide benefits to both the patient and the physician.

SUMMARY OF THE INVENTION

The abdominal tissue support of the invention solves many of the above discussed problems. The present invention generally includes a waist belt, at least one support apron affixed to one side of the waist belt, and a shoulder strap arrangement. Optionally the invention may include a second movable support apron, slideable along the length of the waist belt for positioning on the other side of the waist belt relative to the first support apron In a preferred embodiment, the waist belt may be at least partially covered with a hook and loop fastener material such as Velcro® with the loop portion of the fastener material arranged to face the patient's skin for patient comfort. The first support apron is operably fixedly secured to the waist belt and the waist belt extends through a sleeve formed at the bottom of the movable support apron. The exterior of the waist belt may be at least partially covered with a hook material of the hook and loop fastener to engage and attach to the loop portion of the hook and loop fastener on the interior of the waist belt.

In one embodiment, the first support apron is secured to a first end of the waist belt such as by stitching. The first support apron may be substantially triangular in shape and may include a vertical strap and a diagonal strap that provides additional structural support generally proximate a lower and outer portion. The first support apron may include a fabric apron portion, which fills in the space between the vertical strap, the diagonal strap and the waist belt. Alternately, the space enclosed by the vertical strap, the diagonal strap and the waist belt may be left open or may be partially filled with mesh or a matrix of straps. The first support apron preferably includes a shoulder strap extending upwardly and away from the first support apron. The shoulder strap may be an extension of the vertical strap and may be formed from a hook and loop fastener type material such as Velcro®. The shoulder strap may be adapted to support the waist belt by passing over the patient's shoulder or neck or may be adapted to be secured to a fixture that is mounted on a procedure table in the vicinity of the patient's head or at another convenient location within the procedure suite.

The movable support apron, if present, is slideably secured to the waist belt such as by a sleeve located along the bottom edge of the movable support apron. The movable support apron may include a vertical strap and a diagonal strap generally proximate a lower and outer portion and may be substantially triangular in shape with the sides of the triangle being generally formed by the sleeve, the vertical strap, and the diagonal strap. The movable support apron may include a fabric filling in the space surrounded by the vertical strap and the diagonal strap and the sleeve or may be partially filled or may be left open. The movable support apron may include a pad of hook fastener material in the vicinity of the meeting of the vertical strap and the diagonal strap.

The shoulder strap, which extends upwardly from the first support apron and may be an extension of the vertical strap of the first support apron, preferably is formed of a loop portion of a hook and loop fastener material and is adapted to interconnect with the hook material pad on the movable support apron.

The first support apron and the movable support apron may be formed of a non-woven fabric. It is preferred that the fabric used to form the first support apron and movable support apron be a non-shedding fabric with limited stretch that does not produce significant lint fibers and/or other particulate matter that may interfere with the maintenance of a sterile surgical field. The fabric used to form first support apron and movable support apron may be an inexpensive or biodegradable fabric in order to allow for disposable use of the abdominal tissue support. The abdominal tissue support is primarily intended for use on a patient who is positioned supine, typically on a surgical table.

In operation, the abdominal tissue support is preferably placed on the table prior to the patient being positioned on the table, with the waist belt disconnected and the movable support apron positioned to one side of the patient while the first support apron is positioned to the other side of the patient.

Once the patient is positioned supine, lying on top of the waist belt with the first support apron on one side and the movable support apron on the other side. The waist belt is wrapped around the patient as low on the abdomen as possible, in the vicinity of the femoral crease. The waist belt may then be secured to the first support apron and to itself by engagement of the pads of hook and loop fastener material for example. The hook and loop fastener material may extend a substantial distance along the waist belt in order to provide a secure attachment, even if a large amount of tissue is to be supported as well as to allow adjustability.

The first support apron preferably should be positioned so as to be above one thigh of the patient. The movable support apron can then be slid along the waist belt to position it above the other thigh of the patient. The shoulder strap is then placed under tension and routed up over the patient's torso and over one of the patient's shoulders. In this embodiment, the route of the shoulder strap continues down diagonally across the back and out under one of the patient's armpits and is then extended to be attached to the hook material pad on the movable support apron. Alternately, the shoulder strap may be attached to a fixture located near the head of the patient. The shoulder strap and the movable support apron are both placed under tension in a direction upward and away from the femoral crease in order to lift the excess abdominal tissue away from the femoral crease. Once the first support apron and the movable support apron are in the desired position, supporting the excess abdominal tissue away from the femoral crease, the shoulder strap is secured relative to the movable support apron so that the excess abdominal tissue is held up and away from the femoral crease to allow access for the femoral puncture. The location of the shoulder strap attachment may be on the movable support apron as well and the location of the hook pad for attaching the shoulder strap, for example, may be reversed to be on the first support apron if desired.

Once the femoral puncture procedure is completed, the shoulder strap may be released from its attachment on the movable support apron. The waist belt may be released and the surgical tissue support may be discarded.

DETAILED DESCRIPTION OF THE INVENTION

Figure 1:
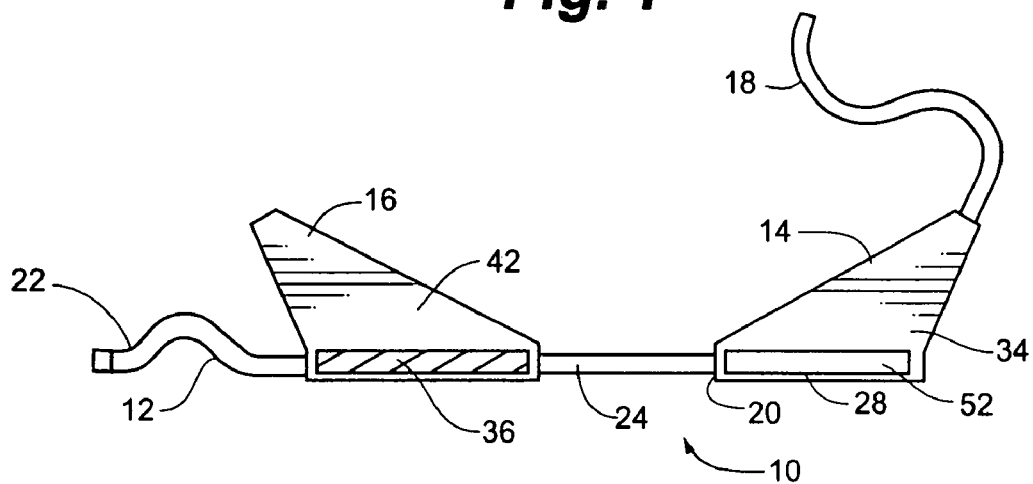
FIG. 1 is a plan view of a surgical tissue support in accordance with the present invention viewed from the inside.
Figure 2:
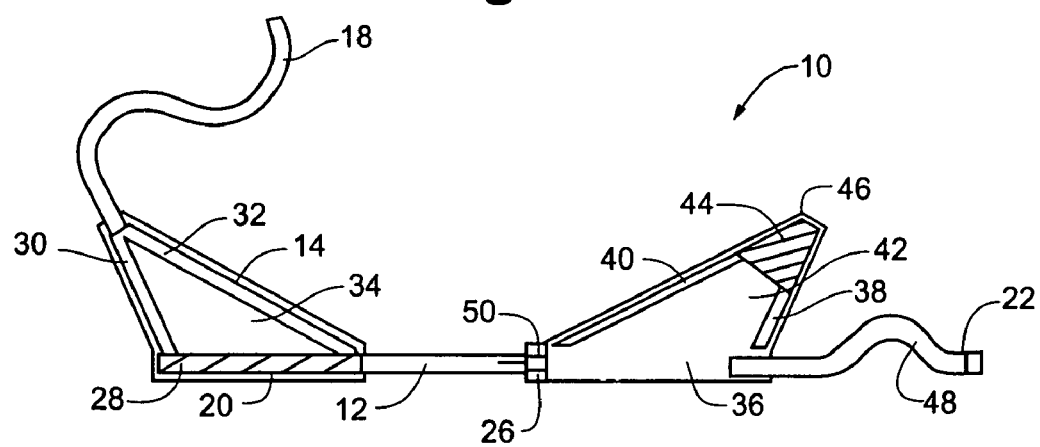
FIG. 2 is a plan view of the surgical tissue support viewed from the outside

Referring to FIGS. 1, 2, 7 and 8, the abdominal tissue support 10 of the present invention generally includes waist belt 12, first support apron 14, optional second movable support apron 16, and shoulder strap 18.

Waist belt 12 generally includes secured end 20 and free end 22. Secured end 20 is operably secured to first support apron 14 such as by stitching, adhesive, fusing, riveting, stapling or other methods known to those skilled in the art. Waist belt 12 is preferably formed of a flexible stretch resistant material, such as fabric, that includes the hook portion of a hook and loop type fastener. In an exemplary embodiment, waist belt 12 may have a width of approximately five centimeters and a length of approximately two meters. The width and length of waist belt 12 may be adjusted as necessary to accommodate patients of different sizes.

In a preferred embodiment, first support apron 14 is secured to waist belt 12 such as by stitching, fusing or adhesives. First support apron 14 may be a substantially triangular structure. Waist belt 12 has a front side 24 and a back side 26. For the purposes of this application, front side 24 will be defined as the side of abdominal tissue support 10 that faces away from the patient's skin and back side 26 will be defined as the side of abdominal tissue support 10 that makes contact with the patient's skin. Throughout this application hook and loop fasteners will be described as preferred embodiments for making operably releasable connections between the various parts of abdominal tissue support 10. It is to be understood that hook and loop fasteners may be replaced with buckles, snaps, adhesives or other forms of operably releasable connecting apparatus known to those skilled in the art and that this disclosure is intended to cover those types of operably releasable connecting apparatus as well as hook and loop fasteners. In addition, non-releasable fasteners such as adhesive may be utilized in which case the abdominal tissue support may be cut to release it from the patient for removal.

In one embodiment, fixed apron 14 includes waist belt portion 28, vertical strap 30, and diagonal strap 32. Optionally first support apron 14 may include fabric panel 34. If present, fabric panel 34 joins waist belt portion 28 to vertical strap 30 and diagonal strap 32 filling in the opening therebetween. First support apron 14 may also be secured to shoulder strap 18. Shoulder strap 18 may be an extension of vertical strap 30 or diagonal strap 32. Shoulder strap 18 may be secured in the vicinity where vertical strap 30 meets diagonal strap 32. Alternately shoulder strap 18 may be secured to movable support apron 16 and be detachably securable to first support apron 14 or detachably secured to both movable support apron 16 and first support apron 14.

Movable support apron 16 generally includes waist belt sleeve 36, vertical strap 38 and diagonal strap 40. Optionally, movable support apron 16 includes fabric panel 42 which occupies the space between waist belt sleeve 36, vertical strap 38 and diagonal strap 40. On front side 24, movable support apron 16 may include shoulder strap securement 44. Shoulder strap securement 44 may take the form of a hook and loop fastening material, a buckle, adhesive or other device for securing shoulder strap 18 to movable support apron 16. Shoulder strap securement 44 may include shoulder strap pad 46 formed of hook and loop material. Shoulder strap securement 44 is desirably located in the area where vertical strap 38 joins diagonal strap 40.

On the back side 26 of movable support apron 16 is waist belt pad 48. Waist belt pad 48 may be formed of the loop side of hook and loop material or adhesive or other material for securing waist belt sleeve 36 to waist belt 12. Waist belt sleeve 36 may include an extended portion 50. Extended portion 50 may extend behind waist belt 12 and have on its back side 26, waist belt pad 48.

Waist belt portion 28 of first support apron 14 may include hook securement portion 52. Hook securement portion 52 may be formed of a hook portion of a hook and loop type fastener and be adapted to receive waist belt pad 48 or hook and loop material secured to waist belt 12.

Figure 3:
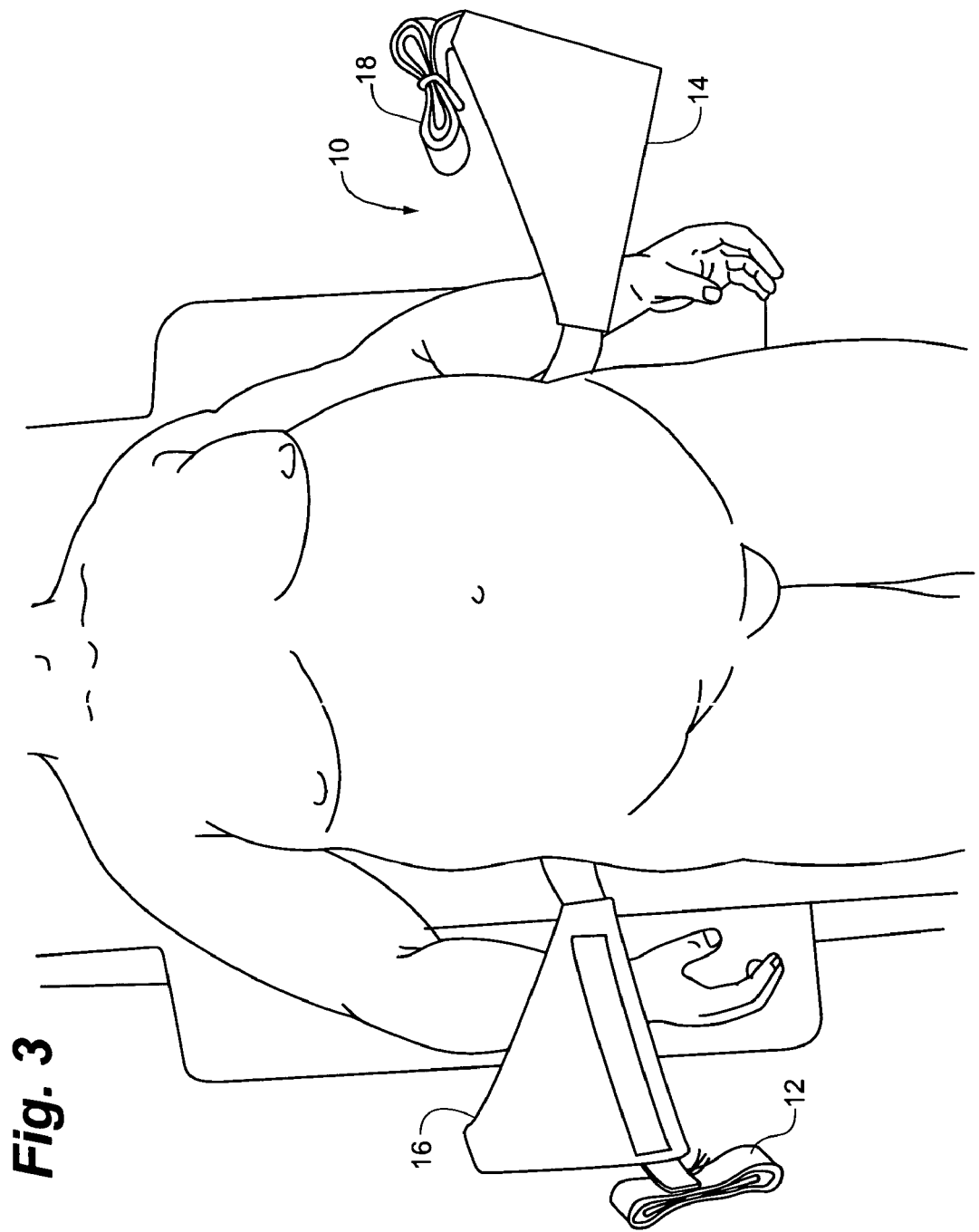
FIG. 3 is a perspective view of a first step of the application of a surgical tissue support to a patient in accordance with the present invention.
Figure 4:
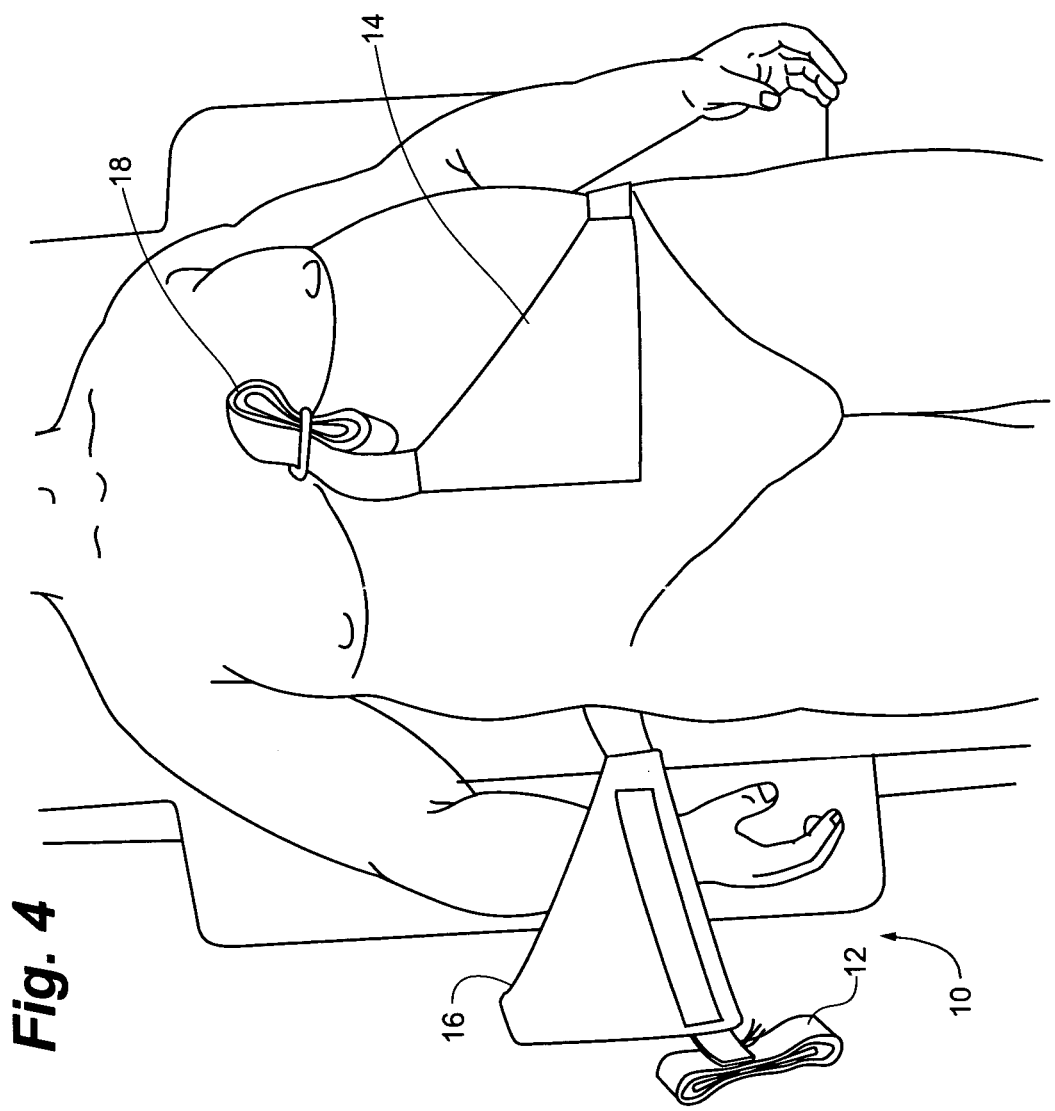
FIG. 4 is a perspective view of a second step of the application of the surgical tissue support to a patient.
Figure 5:
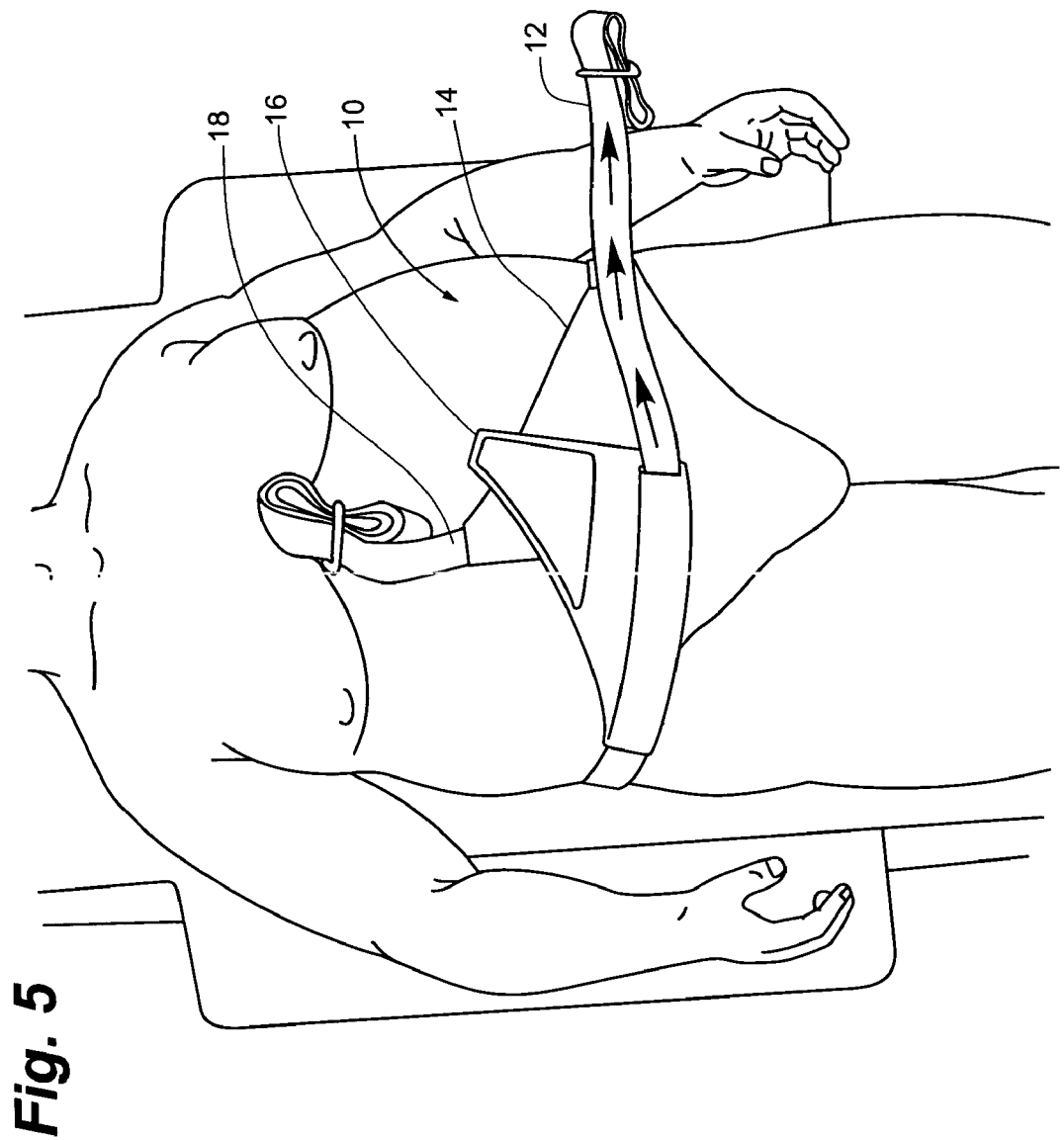
FIG. 5 is a perspective view of a third step of the application of the surgical tissue support to a patient.

In a preferred mode of operation, depicted in FIGS. 3-6 abdominal tissue support 10 is placed on a procedure table so that waist belt 12 crosses the operating table and first support apron 14 is draped over one side of the operating table while movable support apron 16 is draped over the opposite side of the operating table. A patient is then placed on the procedure table, as depicted in FIG. 3, so that the patient is in a supine posture with waist belt 12 behind the patient's back at about the waist. Waist belt 12 is then adjusted in position, as depicted in FIG. 4, so that first support apron 14 is on the patient's abdomen just above the femoral crease and movable support apron 16 is on the patient's abdomen on the other side of the body just above the femoral crease. Referring to FIG. 5, waist belt 12 is secured about the patient snuggly by applying the hook and loop fastener material on waist belt 12 to hook and loop fastener material in the vicinity of waist belt portion 28 on first support apron 14.

Alternately, abdominal tissue support 10 may be applied to patient while the patient is standing and then adjusted before or after the patient assumes a reclining posture on a procedure table.

Figure 6:
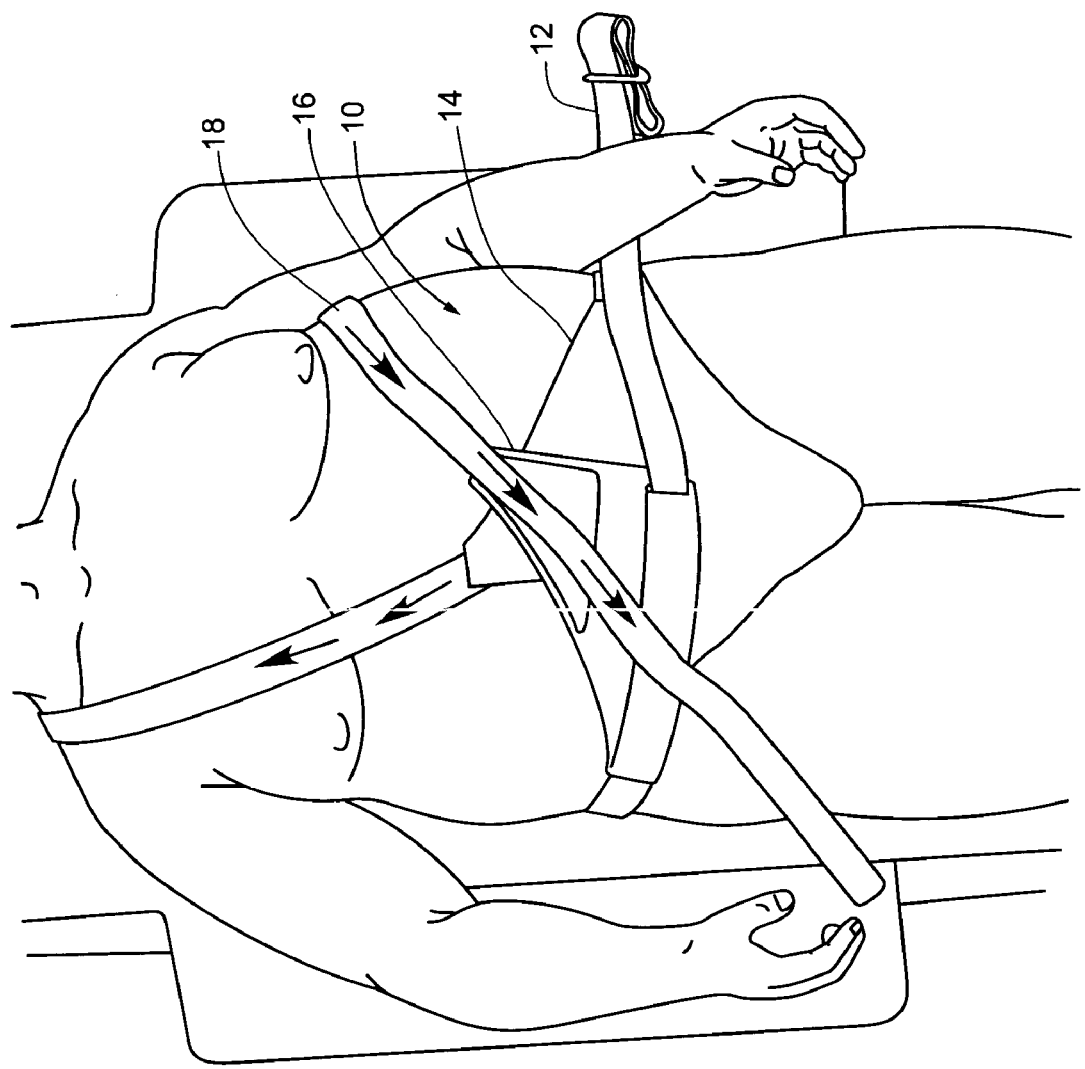
FIG. 6 is a perspective view of a fourth step of the application of the surgical tissue support to a patient.
Figure 7:
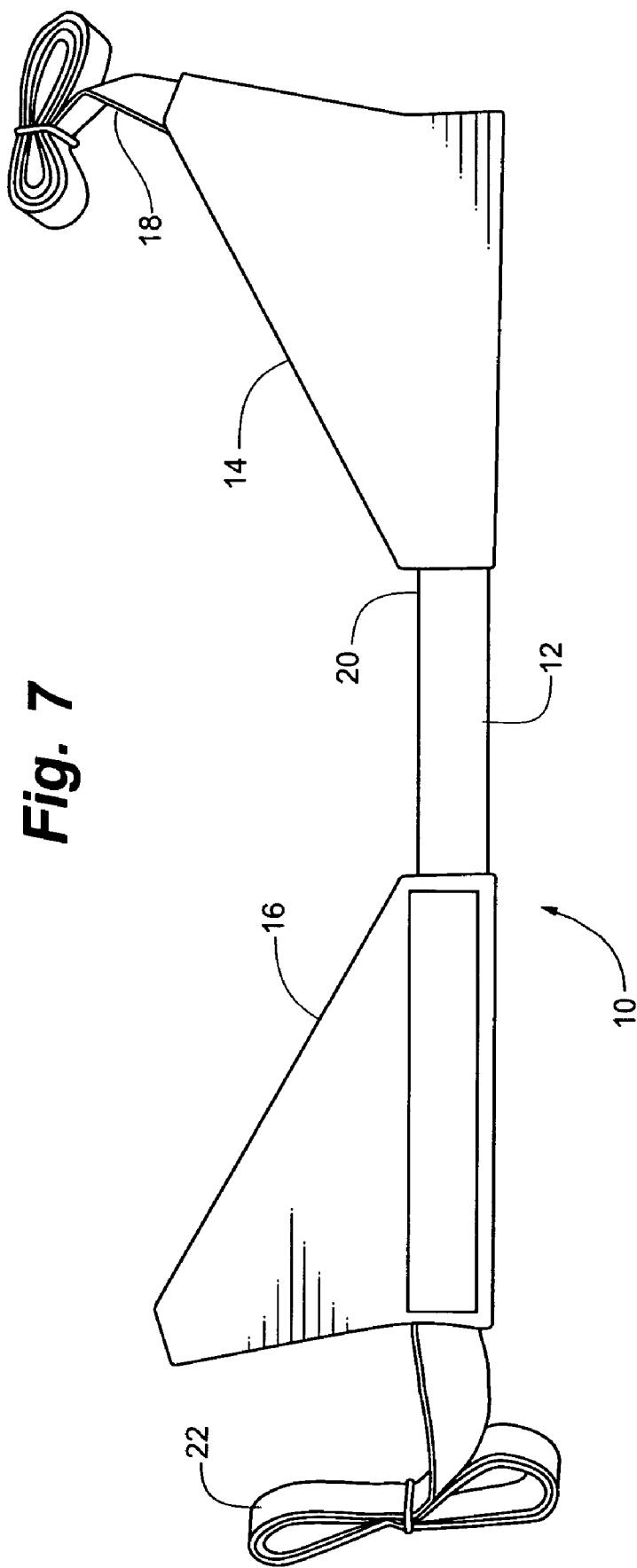
FIG. 7 is a perspective view of a surgical tissue support in accordance with the present invention with a waist belt and a shoulder strap arrangement coiled and not connected.
Figure 8:
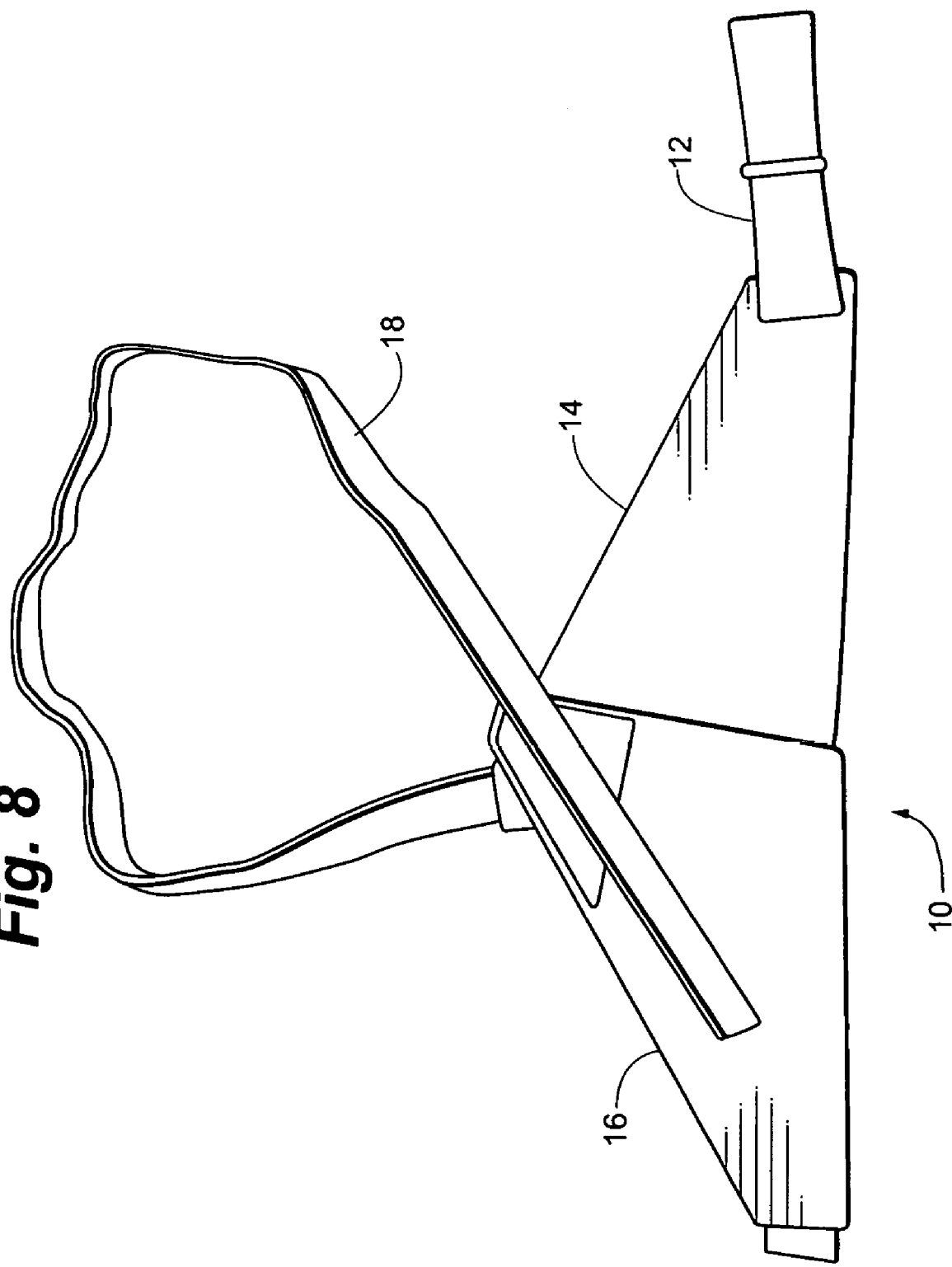
FIG. 8 is a perspective view of a surgical tissue support with the waist belt and shoulder strap arrangement extended and attached as they would be when applied to a patient.

Tension is then applied to shoulder strap 18 to lift excess tissue supported by first support apron 14. Tension is applied on shoulder strap 18 substantially in the direction of the patient's head. Shoulder strap 18 is then routed over the ipsalateral shoulder to first support apron 14 around the back and emerges beneath the contralateral arm of the patient, as depicted in FIG. 6. Alternately, shoulder strap 18 is secured to a fixture near the patient's head. Shoulder strap 18 is further routed to shoulder strap securement 44 on movable support apron 16. Tension is applied to movable support apron 16 in the direction of the patient's head to lift excess tissue away from the femoral crease. Shoulder strap 18 is then secured to shoulder strap securement 44 to support excess tissue via first support apron 14 and movable support apron 16 to provide access to the femoral crease with a femoral puncture procedure.

Once the femoral puncture procedure is completed, abdominal tissue support 10 may be removed and discarded.

The present invention may be embodied in other specific forms without departing from the central attributes thereof, therefore, the illustrated embodiment should be considered in all respects as illustrative and not restrictive, reference being made to the appended claims rather than the foregoing description to indicate the scope of the invention.

What is claimed is:

1. An abdominal tissue support to assist in maintaining a sterile field proximate a patient's groin and upper thigh during femoral puncture procedures for patients that have excess abdominal tissue, the abdominal tissue support comprising:
   an adjustable waist belt having a top edge and a bottom edge dimensioned to encircle the patient's body at a location proximate the waist and anatomically inferior to the excess abdominal tissue;
   a first support apron operably fixedly connected to the waist belt, the first support apron including a portion extending upwardly away from the top and bottom edges of the waist belt;
   a second support apron operably movable along and connectable to the waist belt, the second support apron including a portion extending upwardly away from the top and bottom edges of the waist belt; and
   an apron strap arrangement having a first end and a second end, the first end operably connected to at least one of the first and second support aprons and adapted to lift the at least one of the first and second support aprons upwardly toward the patients upper body when the strap arrangement is selectively secured at a location near or about the patient's upper body whereby the excess abdominal tissue is moved away from the sterile field.

2. The abdominal tissue support as recited in claim 1, in which the second movable support apron operably is slidably connected to the waist belt.

3. The abdominal tissue support as recited in claim 2, in which the apron strap arrangement further comprises hook and loop fasteners and is secured to at least one of the first support apron or the second support apron thereby.

4. The abdominal tissue support as recited in claim 1, in which at least one of the first support apron or the second support apron comprises a vertical strap and a diagonal strap and is substantially triangularly shaped.

5. The abdominal tissue support as recited in claim 4, in which at least one of the first support apron or the second support apron comprises a fabric panel.

6. The abdominal tissue support as recited in claim 1, in which the second support apron further comprises a waist belt sleeve through which the waist belt passes.

7. The abdominal tissue support as recited in claim 1, in which the apron strap arrangement is a shoulder belt structured to extend over the patient's shoulder or around the patient's neck and to secure the first support apron to the second support apron thereby tensioning both the first support apron and the second support apron toward the patient's head and drawing the waist belt toward the patient's head.

8. The abdominal tissue support as recited in claim 1, in which the waist belt further comprises hook and loop fasteners and is securable about the patient's abdomen thereby.

9. A method of assisting in the maintenance of a sterile field and access to a puncture site for the performance of a femoral puncture procedure when a patient has excess abdominal tissue, the method comprising the steps of:
   placing the patient on a procedure table in a supine posture;
   encircling the patient's lower abdomen proximate the waist with an adjustable waist belt having two ends and a top edge and a bottom edge, the waist belt including a first support apron operably connected thereto, the first support apron including a portion extending upwardly away from the top and bottom edges of the waist belt and a second support apron operably movable along and connectable to the waist belt, the second support apron including a portion extending upwardly away from the top and bottom edges of the waist belt and being connectable to an apron strap arrangement having a first end and a second end;
   connecting the two ends of the waist belt that includes a first support apron such that the belt is at a location anatomically inferior to the excess abdominal tissue;
   attaching the first end of the strap arrangement to at least one of the first support apron or the second support apron;
   applying a superiorly directed force to the strap arrangement to displace at least the first support apron or the second support apron and the excess abdominal tissue away from the sterile field and the puncture site.

10. The method as claimed in claim 9, further comprising the step of securing the strap arrangement to a fixture located superior to the waist belt.

11. The method as claimed in claim 9, further comprising the step of securing the strap arrangement about the patient's shoulder or neck.

12. The method as claimed in claim 9, further comprising the steps of utilizing a second support apron operably movable along and connectable to the waist belt;
attaching the strap arrangement to the movable support apron applying a superiorly directed force to the strap arrangement to displace the movable support apron and the excess abdominal tissue away from the sterile field and the puncture site.

13. An abdominal tissue support to assist in maintaining a sterile field at a femoral puncture site proximate a patient's groin and upper thigh during femoral puncture procedures for patients that have excess abdominal tissue, the abdominal tissue support comprising:
means for encircling the patient's body having a top edge and a bottom edge at a location proximate the waist and anatomically inferior to the excess abdominal tissue;
first means for supporting tissue operably fixedly connected to the waist belt, the first means for supporting tissue including a portion extending upwardly away from the top and bottom edge of the means for encircling;
second means for supporting tissue operably movable along and connectable to the means for encircling, the second means for supporting tissue including a portion extending upwardly away from the top and bottom edge of the means for encircling; and
means for tensioning operably connected to at least one of the first and second means for supporting tissue and having a first end and a second end and adapted to move the first and second means for supporting tissue upwardly toward the patient's upper body when the means for tensioning is selectively secured at a location near or about the patient's upper body whereby the excess abdominal tissue is moved away from the sterile field and femoral puncture site.

14. The abdominal tissue support as recited in claim 13, in which the second means for supporting tissue is operably slidably connected to the means for encircling.

15. The abdominal tissue support as recited in claim 13, in which at least one of the first or the second means for supporting tissue comprises a vertical strap and a diagonal strap and is substantially triangularly shaped.

16. The abdominal tissue support as recited in claim 15, in which at least one of the first means for supporting tissue or the second means for supporting tissue comprises a fabric panel.

17. The abdominal tissue support as recited in claim 13, in which the second means for supporting tissue further comprises a sleeve through which the means for encircling passes.

18. The abdominal tissue support as recited in claim 13, in which the means for tensioning is a shoulder belt structured to extend over the patient's shoulder or around the patient's neck and to secure the first means for supporting tissue to the second means for supporting tissue thereby tensioning both the first means for supporting tissue and the second means for supporting tissue toward the patient's head and drawing the means for encircling toward the patient's head.

19. An abdominal tissue support to assist in maintaining access to a femoral puncture site and a sterile field proximate a patient's groin and upper thigh during femoral puncture procedures for patients that have excess abdominal tissue, the abdominal tissue support comprising:
an adjustable waist belt having a top edge and a bottom edge dimensioned to encircle the patient's body at a location proximate the waist and anatomically inferior on the excess abdominal tissue;
a second support apron operably movable along and connectable to the waist belt, the second support apron including a portion extending upwardly away from the top and bottom edges of the waist belt and being connectable to the apron strap arrangement;
at least a first support apron operably fixedly connected to the waist belt, the first support apron including a portion extending upwardly away from the top and bottom edges of the waist belt; and
an apron strap arrangement having a first end and a second end, the first end operably connected to the first support apron and adapted to tension the first support apron upwardly toward the patients upper body when the strap arrangement is selectively secured at a location near or about the patient's upper body whereby the excess abdominal tissue is moved upwardly and away from the sterile field.

20. The abdominal tissue support as recited in claim 19, in which at least one of the first support apron or the second support apron comprises a vertical strap and a diagonal strap and is substantially triangularly shaped.

21. The abdominal tissue support as recited in claim 20, in which at least one of the first support apron or the second support apron comprises a fabric panel.

22. The abdominal tissue support as recited in claim 19, in which the second support apron further comprises a waist belt sleeve through which the waist belt passes.

23. The abdominal tissue support as recited in claim 19, in which the apron strap arrangement is a shoulder belt structured to extend over the patient's shoulder or around the patient's neck and to secure the first support apron to the second support apron thereby tensioning both the first support apron and the second support apron toward the patient's head and drawing the waist belt toward the patient's head.

24. The abdominal tissue support as recited in claim 19, in which the waist belt further comprises hook and loop fasteners and is securable about the patient's abdomen thereby.

25. The abdominal tissue support as recited in claim 19, in which the apron strap arrangement further comprises hook and loop fasteners and is secured to at least one of the first support apron or the second support apron thereby.

* * * * *